United States Patent
Greig et al.

(10) Patent No.: US 6,410,747 B1
(45) Date of Patent: Jun. 25, 2002

(54) HIGHLY SELECTIVE BUTYRYLCHOLINESTERASE INHIBITORS FOR THE TREATMENT AND DIAGNOSIS OF ALZHEIMER'S DISEASE AND DEMENTIAS

(75) Inventors: Nigel H. Greig, Phoenix; Qian-Sheng Yu, Baltimore; Arnold Brossi, Bethesda; Timothy T. Soncrant, Silver Spring, all of MD (US); Marvin Hausman, Stevenson, WA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/254,494

(22) PCT Filed: Jul. 9, 1998

(86) PCT No.: PCT/US98/14063

§ 371 (c)(1),
(2), (4) Date: Jun. 17, 1999

(87) PCT Pub. No.: WO99/02154

PCT Pub. Date: Jan. 21, 1999

Related U.S. Application Data
(60) Provisional application No. 60/052,087, filed on Jul. 9, 1997.

(51) Int. Cl.[7] .............................................. C07D 487/04
(52) U.S. Cl. .................................................... 548/429
(58) Field of Search ........................ 514/411; 548/429

(56) References Cited

U.S. PATENT DOCUMENTS

| | | | | |
|---|---|---|---|---|
| 4,791,107 A | * | 12/1988 | Hamer et al. ............. | 514/228.2 |
| 5,171,750 A | * | 12/1992 | Brossi et al. ............... | 514/411 |
| 5,378,723 A | * | 1/1995 | Brossi et al. ............... | 514/411 |
| 5,409,948 A | * | 4/1995 | Grieg et al. ................ | 514/411 |

OTHER PUBLICATIONS

D'Mello, G.D. et al, Cognitive Brain Research, 3, 1996, 345–352.*
Bartus, R.T., Experimental Neurobiology, 163, 2000, 495–529.*
Burke, J.R. et al, Postgraduate Medicine, 106, 1999, 85–96.*
Shoulson, I. Science, 282, 1998, 1072–1074.*
Cokugras AN, Tezcan EF, Gen Pharmacol 1997 Nov;29(5):835–8.*
Brzostowska, Malgorzata; He, Xiaoshu; Greig, Nigel H.; Rapoport, Stanley I.; Brossi, Arnold, Med. Chem. Res. (1992), 2(4), 238–46.*
Pei, Xue Feng; Greig, Nigel H.; Bi, Sheng; Brossi, Arnold; Toome, V., Med. Chem. Res. (1995), 5(4), 265–70.*

* cited by examiner

*Primary Examiner*—Mukund J. Shah
*Assistant Examiner*—Thomas C McKenzie
(74) *Attorney, Agent, or Firm*—Gibbons, Del Deo, Dolan, Griffinger & Vecchione

(57) ABSTRACT

A method for preventing or treating cognitive impairments associated with aging or Alzheimer's disease which comprises treating a patient at risk for having the cognitive impairment with an effective amount of a highly selective butyrylcholinesterase inhibitor.

6 Claims, 7 Drawing Sheets

FIG. 1A

| STRUCTURE | NO. | COMPOUNDS | COMPOUND NO. IN REFERENCES |
|---|---|---|---|
| (structure with RHNCO-, CH₃, N-CH₃, N-CH₃) | 1. R=CH₃ | Physostigmine | $1^1$ |
| | 2. R=Ph | Phenserine | $2^1$ $12^2$ |
| | 3. R=o-tolyl | Tolserine | $3^1$ $8^2$ |
| | 4. R=isopropylphenyl | Cymserine | $4^1$ $19^2$ |
| | 5. R=CH₃O-phenyl | 4'-Methoxyphenserine[B] | |
| | 6. R=methylphenyl | 4'-Methylphenserine | $13^2$ |
| | 7. R=2'-isopropylphenyl | 2'-Isopropylphenserine | $18^2$ |
| (structure with RHNCO-, CH₃, N-CH₃, N-H) | 8. R=CH₃ | N¹-Norphysostigmine | $5^1$ |
| | 9. R=Ph | N¹-Norphenserine | $6^1$ |
| | 10. R=o-tolyl | N¹-Nortolserine | $7^1$ |
| | 11. R=isopropylphenyl | N¹-Norcymserine | $8^1$ |
| (structure with RHNCO-, CH₃, N-CH₃, N-Bn) | 12. R=CH₃ | N¹-Benzylnorphysostigmine | $9^1$ |
| | 13. R=Ph | N¹-Benzylnorphenserine | $10^1$ |
| | 14. R=o-tolyl | N¹-Benzylnortolserine | $11^1$ |
| | 15. R=isopropylphenyl | N¹-Benzylnorcymserine | $12^1$ |
| (structure with RHNCO-, CH₃, N-CH₃, N-CH₂CH₂Ph) | 16. R=CH₃ | N¹-Phenethylnorphysostigmine | $13^1$ |
| | 17. R=Ph | N¹-Phenethylnorphenserine | $14^1$ |
| | 18. R=o-tolyl | N¹-Phenethylnortolserine | $15^1$ |
| | 19. R=isopropylphenyl | N¹-Phenethylnorcymserine | $16^1$ |

FIG. 1B

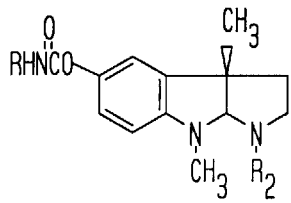

| | | | |
|---|---|---|---|
| 20. $R_1$=$CH_3$, $R_2$=-$CH_2$-CH=$CH_2$ | | $7^3$ | |
| | $N^1$-Allylnorphysostigmine | | |
| 20. $R_1$=$CH_3$, $R_2$=-$\underset{O}{\overset{\|}{C}}$NH$CH_3$ | | $6^3$ | |
| | Eseramine | | |

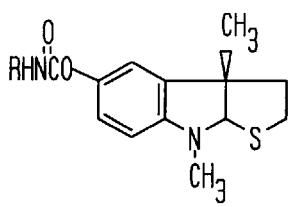

| 22. R=$CH_3$ | Thiaphysovenine | $3^4$ |
|---|---|---|
| 23. R=⌬ | Thiaphenserine | $10^4$ |
| 24. R=⌬-CH₃ | Thiatolserine | $11^4$ |
| 25. R=⌬-iPr | Thiacymserine | $13^4$ |

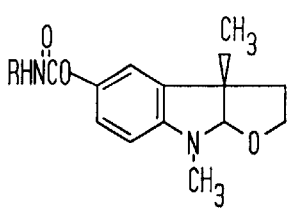

| 26. R=$CH_3$ | Physovenine | $2a^5$ |
|---|---|---|
| 27. R=⌬ | Phensvenine | $9a^5$ |
| 28. R=⌬-CH₃ | Tolsvenine | $11^2$ |
| 29. R=⌬-iPr | Cymsvenine | $10a^5$ |

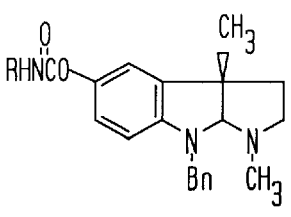

| 30. R=$CH_3$ | $N^8$-Benzylnorphysostigmine | $(-)9^6$ |
|---|---|---|
| 31. R=⌬ | $N^8$-Benzylnorphenserine | $(-)10^6$ |
| 32. R=⌬-CH₃ | $N^8$-Benzylnortolserine | |
| 33. R=⌬-iPr | $N^8$-Benzylnorcymserine | |

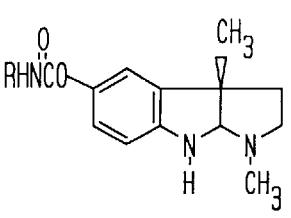

| 34. R=$CH_3$ | $N^8$-Norphysostigmine | $(-)11^6$ |
|---|---|---|
| 35. R=⌬ | $N^8$-Norphenserine | $(-)12^6$ |
| 36. R=⌬-CH₃ | $N^8$-Nortolserine | |
| 37. R=⌬-iPr | $N^8$-Norcymserine | |

FIG. 1C
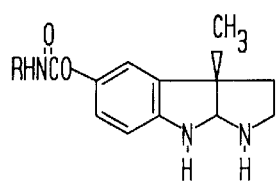
| | | | |
|---|---|---|---|
| 38. R=CH₃ | N¹,N⁸-Bisnorphysostigmine | (-)10⁷ |
| 39. R= phenyl | N¹,N⁸-Bisnorphenserine | (-)9⁷ |
| 40. R= tolyl | N¹,N⁸-Bisnortolserine | |
| 41. R= cumyl | N¹,N⁸-Bisnorcymserine | |
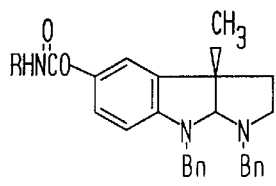
| | | | |
|---|---|---|---|
| 42. R=CH₃ | N¹,N⁸-Bisbenzylnorphysostigmine | (-)19⁷ |
| 43. R= phenyl | N¹,N⁸-Bisbenzylnorphenserine | (-)18⁷ |
| 44. R= tolyl | N¹,N⁸-Bisbenzylnortolserine | |
| 45. R= cumyl | N¹,N⁸-Bisbenzylnorcymserine | |

FIG. 2

Phenserines Alter the Secretion of β-APP In Vitro

Cells: Human Neuroblastoma cells ($1 \times 10^7$, IMR-32)
Conditions: low serum media (0.5% FBS) incubated with drug 2 days
Antibody: 6E10 (residues 1-28 of Aβ)-Shown
22C11 (amino terminal, extracellular domain of β-APP)-6E10 pattern
Anti-HSP-70 (heat shock protein-70)-No different from untreated CNT
Drugs: Phenserine, Tolserine (AChE selective)
Cymserine (BChE selective)

```
1      2    3     4      5     6      7     8
(MW)   CNT  Phenserine  Tolserine    Cymserine
116         5     50     5     50     5    50 μg/ml

95

66              Conditioned media
```

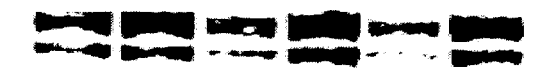

```
1      2    3     4      5     6      7     8
(MW)   CNT  Phenserine  Tolserine    Cymserine
116         5     50     5     50     5    50 μg/ml

95

66              Cell lysate
```

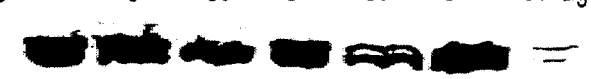

Cymserine protects against a cholinergic forebrain lesion-induces increase in β-APPγ and, additionally, reduces levels in normal animals

HIGHLY SELECTIVE BUTYRYLCHOLINESTERASE INHIBITORS FOR THE TREATMENT AND DIAGNOSIS OF ALZHEIMER'S DISEASE AND DEMENTIAS

This application is a National Stage Application of PCT/US98/14063 which claims priority from US Provisional Application No. 60/052,087, filed Jul. 9, 1997.

BACKGROUND OF THE INVENTION

Defects in the cholinergic system have been suggested to underlie cognitive impairments associated with normal aging and Alzheimer's disease (Bartus et al., Science 217:408–417 (1982); Fisher et al., Neurobiol. Aging 13:9–23 (1992)). Much research has focused on the development of cholinomemetic replacement therapy as a potential treatment of these impairments. Among them, cholinesterase inhibitors, such as physostigmine (Phy) and tetrahydroaminoacridine (ThA) have been investigated for memory-enhancing effects in both animals (Rupniak et al., Neurobiol. Aging 11:09–613; 1990); Murray et al., Psychopharmacology 105:134–136(1991) and human patients (Mohs et al., J. Am. Geriatr. Soc. 3:749–757 (1985); Summers et al., N. Engl. J. Med. 315:1241–1245(1986)).

Other agents have been proposed as selective inhibitors of acetylcholinesterase (AChE). Thus heptyl-physostigmine (Heptyl-Phy) was described as having greater lipophilicity, longer inhibitory action on cholinesterase and more persistent increases in acetylcholine in brain with less toxicity than the parent compound (Brufani et al., Pharmacol. Biochem. Behav. 26:625–629 (1987)). There is concern, however, as to whether the therapeutic window of heptyl-Phy is wide enough for clinical use. Phenserine ((−)-N-phenylcarbamoyl eseroline) has been identified as a superior, selective AChE inhibitor and thus suited as an agent for the therapy for cognitive impairments associated with aging and Alzheimer's disease. (U.S. Pat. No. 5,409,948, issued Apr. 25, 1995).

In U.S. Pat. No. 5,171,750 issued Dec. 15, 1992, a series of substituted phenserines are disclosed which are indicated to be either selective inhibitors of AChE or butyrylcholinesterase (BChE). The cumylcarbamate (4'-isopropylphenylcarbamate) derivative of (−)-physovenol was noted to have a reverse enzyme specificity, i.e., it inhibited BChE selectively over AChE. The patent indicates that the compounds of the invention are useful "for treating cholinergic disorders such as glaucoma, Myasthenia Gravis, Alzheimer's disease and as an antidote against poisoning with organo phosphates." There is no indication as to which type of inhibitor would be used to treat the specified disorders, however, there is a further disclosure to the effect that AChE, which is found in red blood cells, in the brain and in nerve tissues, seems to be more specific an enzyme known to hydrolyze acetylcholine (ACh) in vivo than does BChE which is found in serum, pancreas and the liver. The marked cholinergic loss in AD is accompanied by dramatic reductions in the enzymes cholineacetyl transferase, involved in the synthsis of the cholinergic neurotransmitter acetylcholine, Ach, and of AChE, that ends the action of Ach (Perry, et al. Brit. Med. J., 2 6150: 1457–1459, 1978; Whitehouse, et al. Science 215; 1237–1239, 1982.

U.S. Pat. No. 5,378,723, issued Jan. 3, 1995 describes a series of thiaphysovenol carbamic acid derivatives which are indicated to exhibit high potency in the inhibition of AChE or BChE. The compounds of that invention were indicated, as in the case of U.S. Pat. No. 5,171,750 above, to be useful in treating disorders such glaucoma, Myasthenia Gravis, Alzheimer's disease and poisoning with organo phosphates. As above, no specific indication is given as to which type of inhibitors would be used in which specified disorder.

Geula and Mesulam in a paper entitled "Cholinesterases and the Pathology of Alzheimer's Disease", *Alzheimer's Disease and Associated Disorders*, Vol. 9, Suppl. 2, pp 23–28 (1995) make the following observations in summary: "Alzheimer's Disease (AD) is accompanied by a marked loss of acetylcholinesterase (AChE) activity associated with cortical cholinergic axons and cholinoceptive neurons. Simultaneous with this loss, cholinesterase (ChE) activity emerges in AD cortex in the form of AChE and BChE activity associated with plaques, tangles, and amyloid angiopathy. Our observations have shown that the ChE's associated with the pathological lesions of AD (ADChEs) possess different enzymatic properties and quite possibly are of a different source as compared with the ChEs associated with normal neurons and axons. The ADChEs most likely have noncholinergic functions involved in the pathogenesis of AD." In a further section the authors at p.26 state: "These observations indicate that glia are a likely source of the ChE, and particularly the BChE, associated with the pathological lesions of AD. They also suggest that a high ratio of BChE to AChE positive glia may play a permissible or causative role in the neuropathology of this disease. It is possible that other pools of ChE exist with enzymatic properties similar or identical to those of AD ChEs. This possibility remains unexplored."

Workers in the art have indicated that BChE is found in significantly higher quantities in AD plaques than in plaques from age-matched non-demented brains. Moreover, BChE was found to alter the aggregation of beta amyloid peptide (Aβ). It has been hypothesized that since AChE is inhibited by high concentrations of acetylcholine (ACh), while BChE remains unaffected, it may well be that BChE may play an important role in the in vivo regulation of synaptic concentrations of ACh in the brain of AD patients. BChE inhibitor, instilled into the brain has produced a significant increase in the level of extracellular Ach. (Giacobini, et al., Proc. Soc. Neurosci., 22; 203, 1996.)

It has also been found that in 3 AD specimens plaques, which were of the compact or neuritic type, were almost always associated with intense BChE activity. It was concluded that BChE activity appears at the intermediate stage of plaque formation and that it may therefore constitute one of the factors involved in the transformation of an initially benign Aβ deposit into a compact neuritic form associated with neural degeneration and dementia.

SUMMARY OF THE INVENTION

It has been unexpectedly discovered and thus forms the basis of the present invention that highly selective BChE inhibitors can be utilized by systemic administration to prevent or treat cognitive impairments associated with aging or Alzheimer's disease in a host. Since BChE activity has previously been identified to reside primarily in peripheral organs, such as the pancreas, liver and serum or in the circulation and its inhibition was associated with side effects observed in first generation Alzheimer's disease therapy (Liston et al., Proc. Soc. Neurosci., 20: 608, 1994.) Soreq & Zachnt, Human Cholinestrase and ?, Academic Press, New York, pp. 21–29, 1993) ref), the use of highly selective BChE inhibitors in the treatment or prevention of cognitive impairments associated with aging or Alzheimer's disease was not suggested by the art. A further factor that pointed away from the possible use of highly selective BChE inhibitors in treating cognitive diseases of the brain and CNS was the expected distribution pattern of such agents. Data available in the art suggest that such compounds would be preferentially bound to peripheral organs where the major part of their substrate activity resides. It was, therefore, not expected that clinically useful concentrations of highly selective BChE inhibitors administered systematically to a patient would pass through the blood brain barrier and be available in the brain as (i) such compounds would be expected to be bound to systemic enzyme before reaching the brain, restricting its access, and (ii) most BChE inhibitors known in the art do not readily enter the brain. Indeed, until the present, inhibitors of BChE have been largly utilized as pesticides in agriculture. (Soreq and Zachut, Human Cholinesterases and Anticholinesterases, Academic Press, N.Y., pp. 21–29, 1993).

The term "highly selective" as used herein is meant to include those BChE inhibitors whose ratio of IC (50) values against human plasma BChE compared to their IC (50) values against human erythrocyte AChE were greater than about 15 to 1.

The IC (50) values can be determined for such inhibitors using methods well known in the art. In such assay the pharmacological activity of each compound, as an IC (50), defined as the concentration, in nanomoles, required to inhibit 50% of the enzyme activity of AChE and BChE, is determined separately. For determination of IC (50) values, the enzyme activity of each concentration was expressed as a percent of that determined in the absence of each compound. This then was transformed into a logit format, where logit=In (% activity/[100-% activity]), and was plotted as a function of the log concentration of the compound. IC (50) values (i.e., logit=In (50/[100−50]=0) were determined only from correlation coefficients ($r^2$) of less than −0.985 and when more than 50% inhibition was achieved from duplicate samples. The selectivity ratio is then determined by comparing the IC (50) values obtained for each compound with AChE to that for BChE.

BRIEF DESCRIPTION OF THE FIGURES

FIGS. 1A, 1B and 1C represent a table of chemical structures of compounds tested for activity and includes compounds with desirable selectivity for BChE in accordance with the present invention.

FIG. 2 is an immunoblot of an assay to determine the effect of indicated compounds on the in vitro secretion of βAPP.

DETAILED DESCRIPTION OF THE INVENTION

Figure 3:
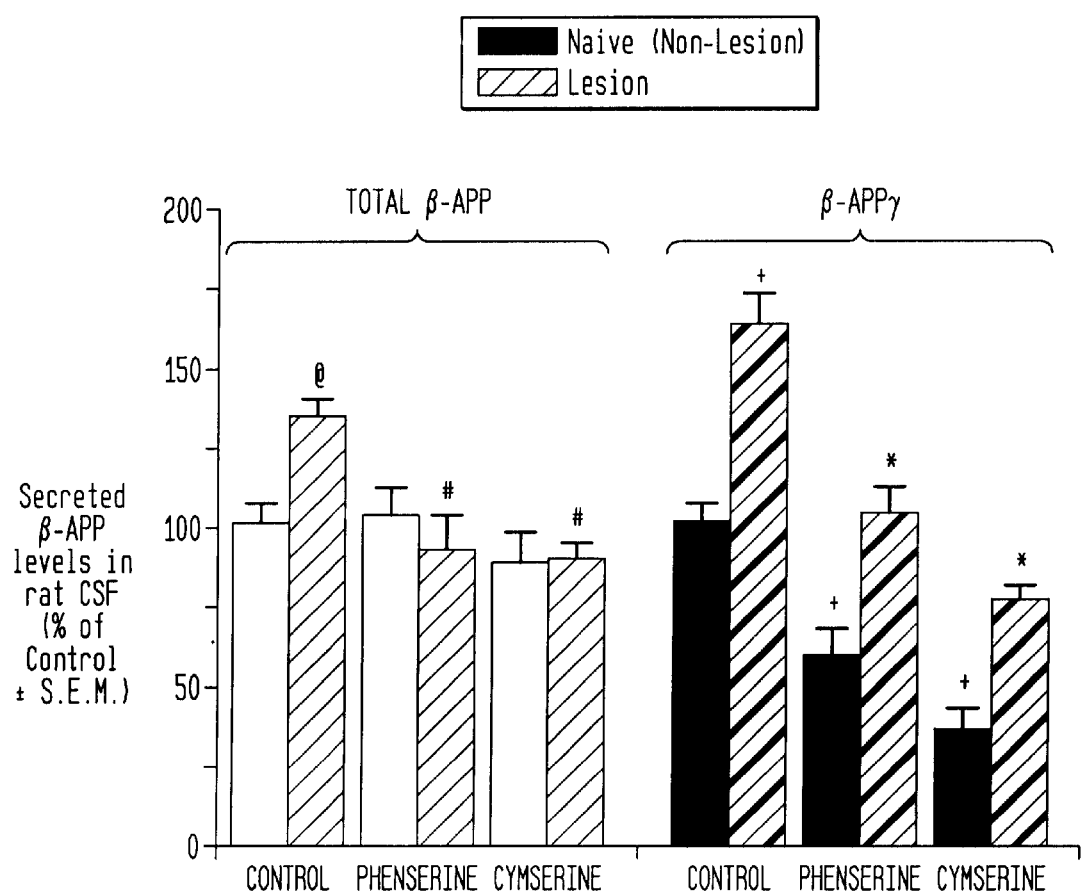
FIG. 3 is a graph demonstrating that cymserine reduces CSF βAPPγ. levels in rats.

The highly selective BChE inhibitors useful in the method of the present invention are those compounds in Table 1 which are indicated to have a selectivity for BChE of 15 or greater, while their structures are provided in FIGS. 1A, 1B and 1C (along with their selectivity ratio) which for compound of the invention again is a selectivity for BChE of 15 or greater. For structural comparison purposes, other related compounds are also shown in Table 1 and FIGS. 1A, 1B, 1C which do not exhibit the desired selectivity for BChE.

Among the compounds listed in Table 1 and FIG. 1 are certain novel compounds which inhibit butyrylcholinesterase. The novel compounds of the invention are (number in parenthesis corresponds to number of compound in Table 1): $N^8$-benzylnorcymserine[33]; $N^8$-norcymserine[37]; $N^1$, $N^8$-bisnorcymserine (41); $N^1$, $N^8$-bisbenzylnorphysostigmine (42); $N^1$, $N^8$-bisbenzylnorphenserine (43); and $N^1$, $N^8$-bisbenzylnorcymserine (45). These novel compounds were synthesized as follows:

(−)-(3aS)-8-Benzyl-1,3a-dimethyl-1,2,3,3a,8,8a-hexahydropyrrolo[2,3-b]indol-5-yl-N-4'-isopropylphenylcarbamate ($N^8$-Benzylnorcymserine; compound 33).

(−)-(3aS)-8-Benzyl-1,3a-dimethyl-1,2,3,3a,8,8a-hexahydropyrrolo[2,3-b]indol-5-ol[1] (33 mg, 0.112 mmol) was dissolved in ether (2 mL), and Na (1 mg) was added. The mixture was stirred at r.t. for 1 min, then 4-isopropylphenylisocyanate (18.1 mg, 0.112 mmol) was added. The mixture was stirred at rt for 5 min. After the removal of solvent, the residue was chromatographed ($CH_2Cl_2$/MeOH=20/1) to give 33 (40 mg, 80.0%) as a foam: $[\alpha]_D$ −60.0° (c=0.2, $CHCl_3$); $^1$H NMR ($CDCl_3$) δ7.40–7.08 (m, 9H, Ar—H), 6.80 (d, J=2.2 Hz, 1H, C4—H), 6.70 (dd, J=2.2, 8.5 Hz, 1H, C6—H), 6.15 (d, J=8.5 Hz, 1H, C7—H), 4.45 and 4.35 (AB, J=16.6 Hz, 2H, Ph—$CH_2$), 4.25 (s, 1H, C8a-H), 2.80 (m, 1H, Ph—CH<), 2.68 (m, 2H, C1—$H_2$), 2.32 (s, 3H,N1—$CH_3$), 1.90 (m, 2H,C2—$H_2$), 1.35 (s, 3H,C3a-$CH_3$), 1.15 (d, J=7.0 Hz, 6H, >$CMe_2$); EI-MS m/z (relative intensity): 294 (MH+—ArNHCO, 65), 280 (2.2), 265 (3.6), 237 (75), 207(58), 160 (34), 91 (100). HR-MS m/z Calcd for $C_{29}H_{33}N_3O_2$: 455.2573; found: 455.2569.

(−)-(3aS)-1,3a-Dimethyl-1,2,3,3a,8,8a-hexahydropyrrolo[2,3-b]indol-5-yl-N-4'-isopropylphenylcarbamate ($N^8$-Norcymerserine; compound 37)

Compound 33 (22 mg, 0.048 mmol) was dissolved in a mixture of MeOH (1 mL), $H_2O$ (1 mL) and TFA (0.5 mL). Palladium hydroxide on carbon (5 mg) was added. The reaction mixture was stirred under hydrogen at atmospheric pressure at r.t. for 1 h, and then the catalyst was filtered. The filtrate was evaporated in vacuo to give a residue which was dissolved in $H_2O$, basified by $Na_2CO_3$, extracted with ether, then dried over $Na_2SO_4$. After removal of solvent, the residue was chromatographed on a preparative TLC (silica gel) ($CH_2Cl_2$=10/1) to give product 37 (12 mg, 65.7%) as gum:

20
[α] D-73.8°(c=0.2, $CHCl_3$);

$^1$HNMR ($CDCl_3$) δ67.30 (d, J=8.5 Hz, 2H, C2'—H and C6'—H), 7.10 (d, J=8.5 Hz, 2H, C3'—H and C5'—H), 6.80–6.70 (m, 2H, C4—H and C6—H), 6.50 (d, J=8.5 Hz, C7—H), 4.65 (s, 1H, C8a-H), 2. 85 (m, 2H, C2—$H_2$), 2.64 (m, 1H, —HC<), 2.48 (S, 3H, N1—$CH_3$), 2.00–1.90 (m, 2H, C3—$H_2$), 1.42 (s, 3H, C3a-$CH_3$), 1.20 (d, J=7.0 Hz, 6H, >$CMe_2$); EI-MS m/z (relative intensity): 204 ($MH^+$—ArNHCO, 99), 189 (25), 174(8.3), 117 (10). HR-MZ m/z Calcd for $C_{22}H_{27}N_3O_2$: 365.2105; found 365.2100.

(−)-(3aS)-1,8-Dibenzyl-3a-methyl-1,2,3,3a,8,8a-hexahydropyrrol[2,3-b]indol-5-yl N-4'-isopropylphenylcarbamate (compound 45)

(−)-(3aS)-1,8-Dibenzyl-3a-methyl-1,2,3,3a,8,8a-hexahydropyrrolo [2,3-b]indol-5-ol[2] (68 mg, 0.18 mmol)

was dissolved in anhydrous ether (2 mL), and a piece of Na metal (approx. 1 mg) was added.

The mixture was stirred at r.t. for 1 min, then 4-isopropylphenylisocyanate (30 mg, 0.18 mmol) was added and stirred for 5 min. Evaporation of solvent gave a crude product 20
which was directly chromatographed to give 45 (89 ma, 991.3%) as a gum

[α] D −44.7° (C=0.5, CHCl$_3$); $^1$H NMR (CDCl$_3$): δ7.29 (d, J=8.5 Hz, 2H, C2'—H and C6'—H), 7.14 (d, J=8.5 Hz, 2H, C3'—H and C5'—H), 6.78 (d, J=2.2 Hz, 1H, C4—H), 6.70(dd, J=2.5, 8.5 Hz, 1H, C6—H), 6.15 (d, J=8.5 Hz, 1H, C7—H), 4.48 (s, 1H, C8a-H), 4.30–4.15 (AB, J=16.6 Hz, 2H, Ph—CH$_2$—N8), 3.73 (s, 2H, Ph—CH$_2$—N1), 2.80 (m, 1H, —HC<), 2.70 (m, 2H, C2—H$_2$), 1.90 (m, 2H, C3—H$_2$), 1.40 (s, 3H, C3a-CH$_3$), 1.15 (d, J=7.0 Hz, 6H); EI-MS m/z (relative intensity): 370 (MH$^+$—ArNHCO—, 1.0), 294 (90), 279 (10), 237 (8.0), 174(95), 160 (92), 132 (60), 104 (55), 91 (100). HR-MZ m/z Calcd for C$_{35}$H$_{37}$N$_3$O$_2$: 531.2888; found 531.2907.

(−)-(3aS)-3a-Methyl-1,2,3,3a,8,8a-hexahydropyrrol
[2,3-b]indol-5-yl N-4'-isopropylphenylcarbamate
(compound 41)

Compound 45 (42 mg, 0.078 mmol) was dissolved in isopropanol (1 mL) and Pd(OH)$_2$/C (5 mg) was added. The reaction mixture was stirred under hydrogen at atmospheric pressure and r.t. for 60 h, then the catalyst was filtered. Evaporation of solvent gave a residue which was chromatographed (CH$_2$Cl$_2$/MeOH=10/1) to give the most polar component, compound 41(14 mg, 51.0%) as a gum:

20
[α] D −71.1° (C=0.3,

CHCl$_3$); $^1$H NMR (CDCl$_3$): δ7.29(d, J=8.5 Hz, 2H, C2'—H and C6'—H), 7.10 (d, J=8.5 Hz, 2H, C3'—H and C5'—H), 6.80 (m, 2H, C4—H and C6—H), 6.55 (d, J=8.5 Hz, C7—H), 5.20 (s, 1H, C8a-H), 2.90 (m, 1H, Ph—CH<), 2.80 (m, 2H, C2—H$_2$), 2.13 (m, 2H, C3—H$_2$), 1.45 (s, 3H, C3a-CH$_3$), 1.18 (d, J=7.0 Hz >CMe$_2$); EI-MS m/z (relative intensity): 190 (MH$^+$—ArNHCO, 98), 174(10), 160(70), 146(100), 133(11), 117 (15), 103 (5.0), 91 (14); HR-MS (NH$_3$) m/z: Calcd for C$_{21}$H$_{25}$N$_3$O$_2$: 351.1948; found: 351.1941.

(−)-3aS)-1,8-Dibenzyl-3a-methyl-1,2,3,3a,8,8a-
hexahydropyrrol[2,3-b]indol-5-yl N-
methylcarbamate [compound 42]

(−)-(3aS)-1,8-Dibenzyl-3a-methyl-1,2,3,3a,8,8a-hexahydro-5-methoxypyrrolo[2,3-b]indole (47.5 mg, 0.13 mol) was dissolved in anhydrous ether (2 ml), and a piece of Na metal (approx. 1 mg) was added. The mixture was stirred at room temperature for 1 min, then methylisocyanate (14.6 mg, 0.26 mmol) was added and the mixture stirred for 10 min. Evaporation of solvent gave a crude product which was directly chromatographed to give 42 (50.0 mg, 90.0% as a gum:

20
[α] D −58.2° (C=0.7,

CHCl$_3$); $^1$H NMR (CDCl$_3$): δ7.40–7.20 (m, 10H, Ar—H), 6.75 (d, J=2.2 Hz, 1H, C4—H), 6.64 (d, J=8.5 Hz, 1H, C6—H), 6.24 (d, J=8.5 Hz, 1H, C7—H), 4.65 (s, 1H, N—H), 4.40 (s, 1H, C8a-H), 4.35–4.20 (AB, J=16.6 Hz, 2H, Ph—CH$_2$—N8), 3.70 (s, 2H, Ph—CH$_2$—N1), 2.80 (d. J=3.9 Hz, 3H, NH—CH$_3$), 2.70 (m, 2H, C2—H$_2$), 1.90 (m, 2H, C3—H$_2$), 1.35 (s, 3H, C3a-CH$_3$); EI-MS, m/z (relative intensity): 370 (MH$^+$—CH$_3$NHCO—,33), 354 (1.5), 279 (8.5), 264 (3.0), 91 (100). Anal. C$_{27}$H$_{29}$N$_3$O$_3$) C, H, N.

(−)-(3aS)-1,8-Dibenzyl-3a-methyl-1,2,3,3a,-8,8a-
hexahydropyrrol[2,2-b]indol-5-yl N-
phenylcarbamate [compound 43]

(−)-(3aS)-1,8-Dibenzyl-3a-methyl-1,2,3,3a,8,8a-hexahydropyrrolo[2,3-b]indol-5-ol (40.7 mg. 011 mmol) was dissolved in anhydrous ether (2 ml), and a piece of Na metal (approx. 1 mg) was added. The mixture was stirred at room temperature for 1 min, then phenylisocyanate (13.1 mg, 0.11 mol) was added and stirred for 5 min. Evaporation of solvent gave a crude produce which was directly chromatographed to give 43 (48 mg, 89.1%) as a gum:

20
[αD −59.1° (C=0.7, (CHCl$_3$); $^1$H NMR (CDCl$_3$): δ7.40–6.90 (m, 15H, Ar—H), 6.75 (d, J=2.5 Hz, 1H, C4—H), 6.73 (d, J=8.5 Hz, 1H, C6—H)m 6.17 (d, J=8.5 Hz, 1H, C7—H), 4.45 (s, 1H, C8a-H), 4.30–4.20 (AB, J=16.6 Hz, 2H, Ph—CH$_2$—N8), 3.72 (s, 2H, Ph—CH$_2$—N1), 2.70 (m, 2H, C2—H$_2$), 1.90 (m 2H, C3—H$_2$), 1.38 (s, 3H, C3a-CH$_3$); EI-MS, m/z (relative intensity): 370 (MH$^+$—PhNHCO—, 31), 354 (1.0), 279 (8.0), 264 (2.0), 91 (100). Anal. (C$_{27}$H$_{29}$N$_3$O$_3$) C, H, N.

The synthesis of the remaining compounds listed in Table 1 are known, and may be found in the references cited for each compound listed in FIG. 1. Each of the publications are hereby incorporated by reference into the disclosure hereof.

In summary of Table 1, extensive studies have demonstrated that whereas the classical anticholinesterase physostigmine (1) possesses no selectivity of inhibitory action between the two enzyme subtypes, acetyl-(AChE) and butyrylcholinesterase (BChE), specific substitutions in the 4' (para) position, (4,5), of the (−)-phenylcarbamate of physostigmine (2) provide compounds with a selectivity for BChE inhibition. This is unexpected as other 4' substitutions, (6), or similar substitution in other positions, such as at the 2' (ortho) position (3,7), provide no selectivity for BChE. Recent studies have shown that 3' substitution likewise does not provide BChE selectivity, for example 3'-methyl-carbamoyl eseroline has an IC$_{50}$ of AChE 27 nM and BChE 165 nM. Indeed, substitution in the 2'-; 2',4'-; 3'-; 2',3'-; 3', 5'-; or 2', 4', 6'-positions do not provide BChE selectivity. Additional studies have demonstrated that, independently, substitutions in the ;N$^1$-position of physostigmine (1), such as N$^1$-norphysostigmine (8), N$^1$-benzylnorphysostigmine (12), N$^1$-phenethylnorphysostigmine (16), and N$^1$-allylnorphysostigmine (20) provide BChE selectivity, compared to physostigmine (1). This is unexpected as other substitutions, such as amines (21), do not. Replacement of the N$^1$ group of physostigmine (1) to provide thiaphysovenine (22) and physovenine (26) also unexpectedly provides a selectivity of inhibitory action for BChE. Yet further studies have demonstrated that, independently, substitution in the N$^8$-position of physostigmine (1), to provide N$^8$-benzylnorphysostigmine (30) and N$^8$-norphysostigmine (34), produce potent and selective inhibitors of BChE. A combination of the described modifications provides compounds [11,15,16,19,25,29,33,37] which exhibit or are expected to exhibit dramatic selectivity for BChE versus AChE inhibitory action. Other useful compounds for the purpose of this invention include compounds [12, 20 and 22].

A particularly preferred compound for use in the method of the present invention is cymserine (Compound 4, Table 1, FIG. 1A). The preference for cymserine is based on its ease of synthesis, the availability of stable salts, and its ability to cross the blood brain barrier.

Compositions for use in the methods of the invention include compositions wherein the active ingredient is contained in an effective amount to achieve its intended purpose. The compounds can be administered in any pharmaceutically acceptable amount, for example, in amounts ranging from 0.001 gram to about 1 gram per kilogram of body weight. Based on the information which is presented herein, the determination of effective amounts is well within the skill of the ordinary practitioner in the art. The compounds are generally used in pharmaceutical compositions (wt %) containing the active ingredient with a carrier or vehicle in the composition in an amount of about 0.1 to 99 wt % and preferably about 25–85 wt %.

Either fluid or solid unit dosage forms can be readily prepared for oral administration. For example, the highly selective BChE inhibitors can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent patients sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

Pharmaceutical compositions for parenteral and suppository administration can also be obtained using techniques standard in the art.

Preferred uses of the compounds according to the invention are as pharmaceutical agents suitable for oral administration. Another preferred use of the compounds is in transdermal parenteral formulations, which are particularly useful in preventing or treating cholinergic disorders such as Alzheimer's disease. Accordingly, compositions suitable for administration to these areas are particularly included within the invention. The above parenteral solutions or suspensions may be administered transdermally and delivered with a skin patch. If desired they may be given by injection in an appropriate vehicle such as sesame oil.

Accordingly, incorporation of the active compounds and a slow release matrix may be implemented for administering transdermally. The compounds may be administered transdermally in amounts of about 0.01 to 99% of the composition and preferably about 25 to 85 wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of blood concentration vs. time profile, increased patient compliance due to elimination of multiple dosing schedules, bypassing the hepatic "first pass" metabolism, avoiding gastrointestinal incompatibilities and providing a predictable and extendible duration of activity. However, the main function of the skin is to act as a barrier to entering compounds. As a consequence, transdermal therapy has been preferred for a limited number of drugs that possess the desirable physiochemical properties for diffusion across the skin barrier. One effective method of overcoming the barrier function of the skin is to include a penetration enhancer in the formulation of the transdermal therapeutic system.

The penetration enhancer is a chemical compound that, when included in a formulation, temporarily increases the permeability of the skin to a drug line allowing more of the drug to be absorbed in a shorter period of time. Several different types of penetration enhancers have been reported such as dimethylsulfoxide, n-decylmethylsulfoxide, N,N-dimethylacetamide, N,N-dimethylformamide, 1-dodecylazacycloheptane-2-one (Azone), propylene glycol, ethanol, pyrrolidones such as N-methyl-2-pyrrolidone (NMP) and surfactants.

The above compounds can be present in the reservoir alone or in combination with pharmaceutical carriers. The pharmaceutical carriers acceptable for the purposes of this invention are the known art carriers that do not adversely effect the drug, the host, or the material comprising the drug delivery device. Suitable pharmaceutical carriers include sterile water, saline, dextrose, dextrose in water or saline, condensation products of castor oil and ethylene oxide combining about 30 to 35 moles of ethylene oxide per mole of castor oil, liquid acid, lower alkanols, oils such as corn oil, peanut oil, sesame oil and the like, with emulsifiers such as mono- or di-glyceride of a fatty acid; or a phosphatide, e.g., lecithin, and the like; glycols, polyalkylene glycols, aqueous media in the presence of a suspending agent, for example, sodium carboxymethyl cellulose, sodium alginate, poly(vinylpyrrolidone), and the like, alone or with suitable dispensing agents such as lecithin, polyoxyethylene stearate, and the like. The carrier may also contain adjutants such as preserving agents, stabilizing agents, wetting agents, emulsifying agents and the like together with penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administrated by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult human. The required dose is considerably less when administered parenterally. Preferably about 0.01 to about 150 milligrams may be administered intramuscularly or transdermally, one or two times a day for an adult human.

Compounds for use in the present invention may be administered topically in amounts of about 0.01 to about 99 wt % of the composition, and preferably about 25 to 85 wt %. The method according to the invention comprises administering an effective amount of a compound according to the invention or an effective amount of a pharmaceutical composition according to the invention to a mammal in need of such treatment.

In the present study we assessed the effects of chronic cymserine treatment (5 days) on performance of aged Fischer-344 (F344) rats (21–22 months old) in a 14-unint T-maze, referre to as the Stone maze. The use of the Stone maze paragigm for this study can be supported by ntwo previous observations: (1) the known involvement of the cholinergic system in performance as demonstrated by pharmacological and lesion studied and (2) the marked age-related decline in performance demonstrated in several rodent strains including the Fischer 344 (F344) strain. The use of the F344 rat for this study is also justified because of documented age-related decline in cholinergic markers in specific brain regions and the demonstrated improvement in memory performance of aged rats from this strain following various cholingeric treatments.

Male F344 rats 21–22 months old were obtained from Harlan-Sprague-Dawley under contract from the National Institute on Aging. They were maintained two per cage in a vivarium at the Gerontology Research Center under specific pathogen free conditions as characterized previously.

As previously described, the Stone maze is constructed of translucent plastic with a grid floor wired for scrambled foot shocks and is surrounded by gray walls to reduce availability of extra-maze cues. The only other apparatus was a straight runway (2 m) used for pretraining. Similar to the maze, the runway was also constructed of translucent plastic, and contained a grid floor wired for scrambled foot shocks, and was surrounded by gray walls.

Beginning on day 1 rats received a single daily i.p. injectioon of either 0.9% NaCl as the saline control group or cymserine tartrate dissolved in saline and given in does of 0.5 and 1.0 mg/kg that continued on days 2–5. On days 3–5 injections were made 30 min prior to behavioral testing.

Beginning on day 2 rats were provided training in one-way active avoidance in the straight runway. On each trial, the rat had to locomote from the start box to the goal box within 10 s to avoid the onset of foot shock (0.8 mA). Rats received 10 trials on day 2 and 10 trials on day 3. Training was terminated when the rat met a performance criteria of eight avoidances within 10 consecutive trials within a maximum of 30 trials. Only rats meeting this criterion were tested in the Stone maze on the next day.

Rats received training in the Stone maze scheduled as a 4-trial session during the morning and afternoon on days 4 and 5. During each trial, the rat had to locomote from a start box to a goal box through five maze segments each separated by guiiltine doors. The reinforcement contingency required the rat to negotiate each segment within 10 s to avoid the onset of mild foot shock (0.8 mA), which was terminated when the animal moved throught he door into the next segment. After entry into succeeding segments, the door from the preceding segment was closed to prevent backtracking. Recorded as deviations from the correct pathway, errors were the primary dependent variable and were counted automatically by a series of infrared sensors connected to a microprocessor. Run time from the start box to the goal was also recorded automatically. The frequency and duration of foot shock were recorded on a mechanically operated clock.

No effects of drug treatment were observed during pretraining. The mean (s.e.m.) avoidances for all rats were 67% (1.7), 65% (2.8), 63% (3.8), and 61% (3.9) for the control, and 1, 2 and 3 mg kg cymserine groups, respectively. A one-way analysis of variance (ANOVA) revealed no significant group difference in this parameter, $F(3,40)<1.0$.

Figure 5:
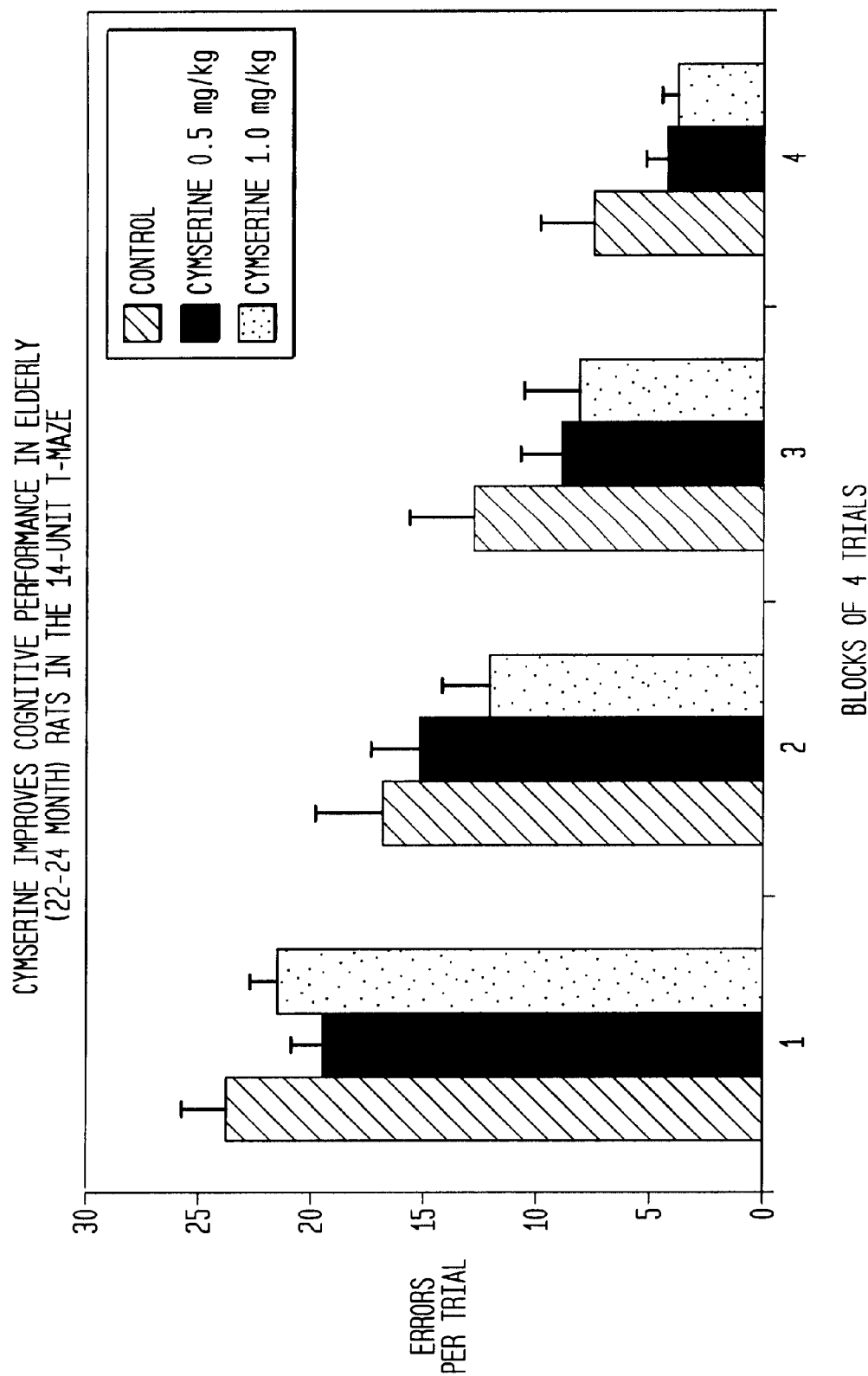
FIG. 5 is a graph illustrating that cymserine improves cognitive performance in rats.

Cymserine treatment significantly reduced the number of errors made in the Stone maze compared with the control condition (FIG. 5). This effect was most prominent during the last blocks of training and appeared least effective for the 3 mg kg dose. Statistical confirmation was provided in the results of a four (drug group) by four (trial block) ANOVA with repeated measures on the last factor. The results yielded a significant main effect of group, $F(3,42)=3.41$, $p=0.03$, a significant main effect of trial block, $F(3,126)=151.6$, $p<0.0001$, but the group by block interaction did not reach statistical significance $F(9,126)=1.55$, $p=0.13$. Thus, individual comparisons of errors were made across all trials. Only the 1 and 2 mg kg groups exhibited significantly improved performance compared with controls.

Other performance variables (runtime, shock frequency and duration) were also reduced in cymersine treated rats to a less consistent degree than observed for errors. The data for each variable were first analyzed in a four (drug) by four (blocks) ANOVA with repeated measures on the last block. No significant main effect of drugs emerged from these analyses; however, the drug x block interaction was significant ($p<0.005$) in each. Thus, the data were analyzed further using t-test comparisons to the control groups at each block. Rats treated with 1.0 mg kg cymserine exhibited significantly reduced run time, shock frequency and duration at blocks 3 and 4 compared with controls. In the 2.0 mg kg group these performance parameters were significantly reduced at block 4. The 3.0 mg kg group was significantly different from controls only for shock duration at block 4. Shock duration was also significantly reduced at block 2 in the 1.0 mg kg group. In summary, these performance variables were significantly affected only during the later trials and most prominently in the 1.0 mg kg group. Some motoric side effects such as fine tremor were detected in a few rats treated with the 3 mg kg dose; otherwise, no side effects were noted in cymserine treated rats.

Chronic treatment with cymserine markedly improved the learning performance of aged rats in the Stone maze. Rats receiving doses of 1–2 mg kg cymserine exhibited significantly reduced errors as well as improvement in other performance variable during the last few trials. this response was presumably due to enhanced cholinergic neutrotransmission by the action of this potent, long-acting cholinesterase inhibitor.

A further aspect of the present invention relates to the discovery that highly selective BChE inhibitors may be used in reducing beta-amyloid precursor protein synthesis and secretion. Alzheimer's disease is characterized by depositions of the amyloid beta-peptide (Aβ) in the form of cerebrovascular amyloid and extracellular senile plaques. The primary core constituent of senile plaques is Aβ peptide, a self-aggregating protein of 39 to 43 residues, which is derived from a group of larger glycosylated transmembrane proteins, β-APPs, of 695 to 770 amino acids. β-APP is the source of the toxic Aβ peptides, known to deposit in the brain of AD patients. Mutations of the APP gene cosegregate with AD in certain families implicating β-APP695 to β-APP770, some of which contain the active Kunitz family of serine protease inhibitor (KPI) domain, as well as Aβ and other amyloidogenic fragments of β-APP as central in the disease process. (Selkoe, J. Neuropathol., Exp. Neurol. 53:438–447, 1994) β-APP is processed/metabolized by alternative proteolytic pathways to generate different breakdown products. These include a secretory and a lysosomal/endosomal pathway. In the secretory pathway, three different secretases have been implicated. In man, but not rat, the majority of β-APP is cleaved within the Aβ region by α-secretase to generate non-amyloidogenic soluble β-APP, sAPP, which is known to possess a number of valued physiological roles. A postulated alternative secretase cleavage, γ-secretase, generates a truncated sAPPγ which contains a potentially amyloidogenic sequence. This is the preferential form produced in the rat, and further cleavage in the human, by a postulated P-secretase, produces the neurotoxin Aβ. (Checler, J. Neurochem., 65:1431–1444, 1995.).

Synthesis, processing and secretion of β-APP and its derivatives occur in vivo in brain, with the products being detectable in brain and CSF in both man and animal models, and, additionally, occurs in vitro in tissue culture with the products being detectable in the conditioned medium of cell cultures and in the cell lysates. Factors that regulate depositions of Aβ are central to understanding the cerebrovascular changes in AD. (Roberson & Harrell, Brain Res. Rev., 25:50–69, 1997.) This disease is also marked by the dramatic loss of cholinergic neurons that project to the cortex and neurochemically by a reduction in presynaptic (choline acetyl transferase, ChAT) markers of the cholinergic system, particularly in the areas of the brain related to memory and learning. (Perry, et al., 1978, ibid.) There is a clear relationship between the loss of cholinergic projections to the cortex and hippocampus and the synthesis and processing of β-APP. (Wallace, et al., PNAS, 98:8712–8716, 1993.) The cholinergic deficits of AD have been modeled in the rat by neurotoxic lesions in the basal forebrain, the most common one being of the nucleus basalis of Meynert (nbM) (Olton and Wenk, In, Psychopharmacology: The Third Generation of Progress (ed, Meltzer) Raven Press, NY, pp 941–954, 1987). Such lesions in rat, like AD in man, lead to a depleted cholinergic system in the cortex of animals and cognitive impairments with features common to AD (Kesner et al., Behav. Neurosci., 101:451–456, 1987). Furthermore, cholinergic forebrain lesions significantly increase the levels of β-APP m-RNA in cortex and secreted β-APP, containing the full length of Aβ, in the CSF of rats (Wallace et al., Mol. Brain Res. 10: 173–178, 1991).

In a report by Lahiri et al., (ANN.NY. Acad. Science, 828:416–421, 1997.) the possibility that the processing of βAPP can be regulated by different cholinesterase inhibitors was investigated. The drugs that were studied in determining the effects of cholinesterase inhibitors on the secretion of secreted forms of βAPP from a number of cell lines, i.e., glioblastoma, HeLa, neuroblastoma and PCI2, included 3,4 diaminopyridine, metrifonate, physostigmine (compound 1, Table 1) and tacrine. The results observed led to the statement that treating neuronal cells with tacrine did regulate the secretion of βAPP, reducing it, while none of the other drugs, all classical anticholinesterases, produced a change in such secretion. It was suggested that any activity shown by these other agents may be independent of their anticholinesterase activity. None of the compounds utilized in these studies was a highly selective BChE inhibitor.

In further studies, the actions of selective AChE (Compounds 2, 3, (phenserine and tolserine) Table 1) and BChE (Compound 4 (cymserine), Table 1) inhibitors were assessed against human neuroblastoma cell lines. Both secreted levels, measured in the conditioned medium, and cellular levels of βAPP, measured in the cell lysates, were assessed and compared to levels achieved in untreated cells. Cymserine dramatically reduced cellular levels of βAPP, indicating a reduced synthesis, and, likewise, reduced secreted βAPP levels (FIG. 2).

A methodology that can be employed to determine the ability of a elected compound to regulate cellular and secreted βAPP levels is as follows:

1 to $1.5 \times 10^7$ of each cell type (neuronal and non-neuronal) are cultured in their respective medium. Before adding drug, the cells are fed with media containing only 0.5% of FBS (low serum). The cells are then incubated either in the absence or presence of the test compound. Following incubation periods from 12 to 48 hours, the conditioned medium from each plate is collected and both it and the cells are centrifuged at 800 g. for 10 minutes. The conditioned medium is collected and the cells lysed in buffer containing 50 mM Tris-Cl (pH 8.0), 150 mM NaCl, 5 mM EDTA, 2 mM PMSF, 0.5% sodium deoxycholate, 1 ug/ml each of aprotonin, leupeptin and TLCK, and 0.1 ug/ml of pepstatin A. The cells are centrifuged for 10 min at 11,000 g at 4° C. Proteins of the supernatant solution (cell lysate) are measured by the Bradford dye-binding procedure (Bradford, Anal. Biochem. 72: 248–254, 1976).

For polyacrylamide gel electrophoresis and immunoblotting: in control experiments, an equivalent concentration of ethanol was used as a vehicle which is less than 1% in media. Compound dosages of from about 0.15 mM to 0.5 mM may be used. 100 uL of conditioned media or 30 ug of protein from the total cell lysate is separated on a 12% polyacrylamide gel containing SDS (SDS-PAGE). Immunoblot analysis was performed using the avidin-biotyinylated complex detection kit of Vector Laboratories as described by Lahiri, et al., J. Neurosci: Res. 12:777–787 (1994). The antisera employed is from the mAb22C11 clone (Boehringer Mannheim) which recognizes all mature forms of βAPP found in cell membranes as well as the carboxyl-truncated soluble forms secreted into the conditioned media and the APP-like protein. Additionally, the mAb6E10 is employed which recognizes residues 1 to 28 of Aβ. To ensure that drug effects are selective to βAPP and do not unselectively affect all proteins, antibody raised against human protease nexin II (PN-II) and anti-HSP-70 (an antibody raised against heat shock protein-70, HSP-70) can be used. Biotinylated secondary antibodies, horse anti-mouse and goat anti-rabbit (Boehringer Mannheim, and Vector Labs) are also used. The above assay method is used to identify which of the highly selective BChE inhibitors of the present invention demonstrate the ability to regulate the synthesis and secretion of secreted and cellular forms of βAPP. As shown in FIG. 2, cymserine can dramatically reduce βAPP levels, and does so when assessed by both mAb 22C11 and 6E10 to βAPP without affecting other secretory proteins, such as HSP-70.

Cymserine, a representative of selective BChE inhibitors, additionally alters βAPP synthesis/processing in vivo. In rats with lesions of the cholinergic forebrain (nucleus basalis of Meynert), levels of βAPP are immediately and dramatically increased in the CSF (FIG. 3, control group with lesion vs. control sham), as a consequence of a depleted presynaptic cholinergic system, modeling AD, and reduced cholinergic projections to higher brain centers in the cortex and hippocampus, as shown previously (Wallace, et al., 1993 & 1995 ibid). Studies have demonstrated that, unlike man, secreted βAPP contains the full length of Aβ, but it is not cleaved by secretase action in rat to produce toxic Aβ peptide (Wallace et al., J. Neurosci., 15:4896–4905, 1995), and hence AD is unique to man, Therefore, in rat, the elevation of βAPP that contains the full length of Aβ peptide, models increased production of Aβ in man.

Figure 4:
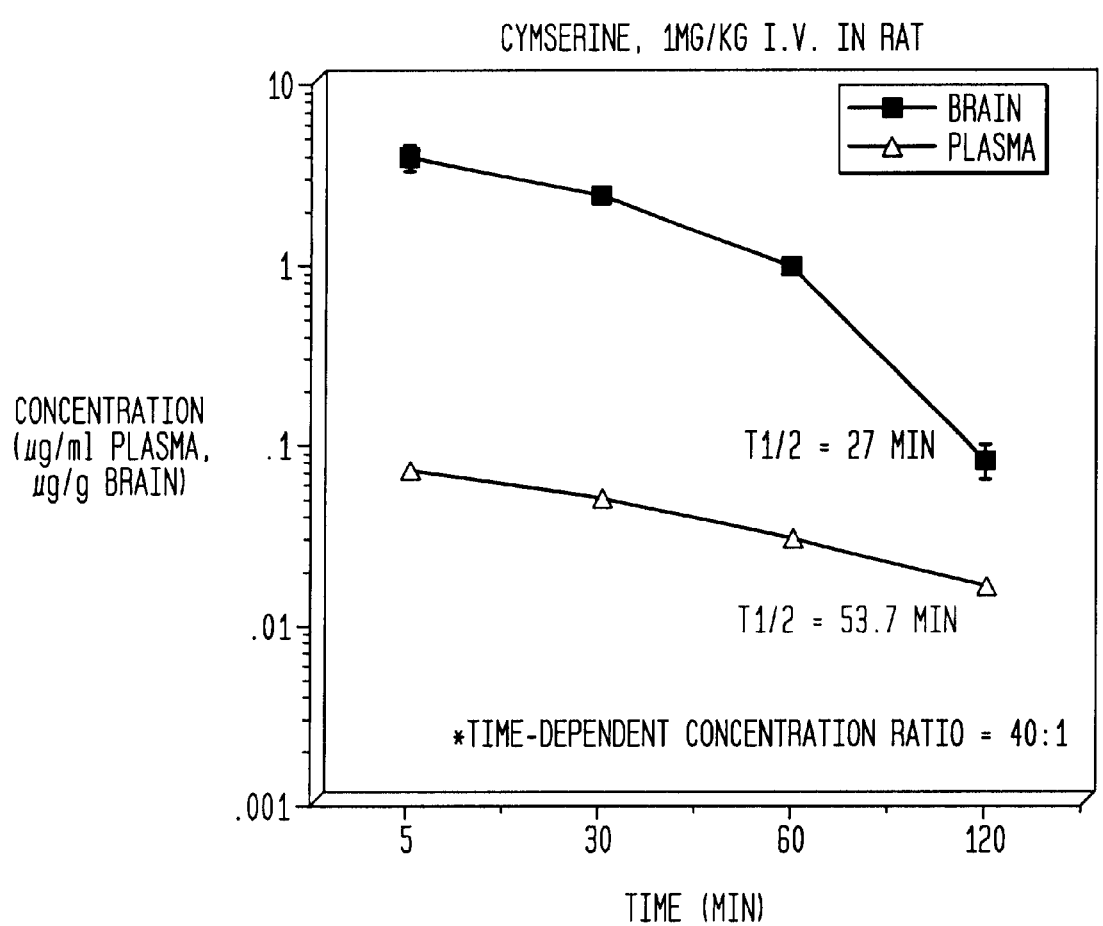
FIG. 4 is a chart showing the blood/brain barrier distribution in a rat over time after administration of 1 mg/kg I.V cymserine.

The administration of cymserine to rats with forebrain cholinergic lesions blocks the elevation of secreted βAPP (FIG. 3). This is in accord with the in vitro action of cymserine on βAPP, and additionally demonstrates that systemically administered cymserine given by the intraperitoneal route twice daily for 7 days, can readily cross the blood-brain barrier and enter brain. Indeed, as shown in FIG. 4, cymserine readily enters and is maintained in brain at levels some 40-fold higher than those in plasma, following its systemic administration (1 mg/kg by the intravenous route). Additionally, as shown in FIG. 3, cymserine reduced levels of βAPP in animals without cholinergic lesions, i.e., in cymserine alone versus pure control rats.

A methodology that can be employed to determine the ability of a selected compound to regulate secreted βAPP levels in vivo is as follows:

For forebrain cholinergic system lesions, rats receive a unilateral subcortical lesion of the nucleus basalis of Meynert (nbM) using N-methyl-D-aspartate (NMDA) as an excitotoxin. In undertaking this, rats are anesthetized and placed in a stereotaxic apparatus with the upper incisor bar set level with the intra-aural line. A 33 gauge infusion cannula is lowered into two sites within the nbM on one side of the brain (AP bregma, ML −2.8 mm, DV −8.0 mm re: skull and AP bregma −0.8 mm, ML −3.0 mm, DV −7.8 mm, respectively). One microliter of a solution of 50 mM NMDA in PBS buffer (physiological pH) is slowly infused into each site. Controls for the lesion are vehicle alone and the contralateral side of NMDA treated animals.

Collection of CSF for analysis of βAPP levels is undertaken by withdrawal of an aliquot from the cistern magna of rats immediately following their death. Quantitation of βAPP is undertaken by immunoblot analysis utilizing mAb 22C11.

Determination of the brain and plasma time-dependent kinetics of cymserine in the rats is undertaken by administering compound into the saphenous vein of anesthetized animals. Animals are killed by excess anesthetic at specific times and blood and brain samples are immediately taken. The blood is centrifuged (10,000 g, 2 min), plasma is collected and, together with the sample of brain, is stored at −80° C. Quantitation of concentrations of cymserine is undertaken by high performance liquid chromatography.

In a further embodiment of the present invention the highly selective BChE inhibitors can be modified by introduction of a fluorescent label and the resulting labeled reagent can be used in histochemical detection of lesions or pathologic states associated with Alzheimer's disease and other dementias on sectioned brain tissue. Any suitable fluorescent label known in the art can be employed, such as, for example, fluorescein. The labeled derivative of the highly selective BChE inhibitor can be prepared in a manner known per se, such as, for example, by reacting such inhibitor with 5-[4,6-dichlortriazen-2-yl-amino]fluorescein and the reaction product can be purified by methods known in the art, such as, for example, thin layer chromatography.

Derivatives of the highly selective BChE inhibitors which can be employed in carrying out brain scans, particularly positron emission tomography and single photon emission tomography, include the following: compounds in Table 1, and analogues thereof, with appropriate moieties to provide them either fluorescence or detection for in vitro or in vivo imaging/quantitation.

Thus the following radiopharmaceutical agents with appropriate modification, if needed, can be attached using methods well known in the art to any of the highly selective BChE inhibitors: thallium, technetium, iodine$^{131}$ or iodine$^{123}$, xenon$^{133}$, krypton$^{481}$, gallium$^{67}$, indium$^{111}$, carbon$^{11}$, nitrogen$^{13}$ and fluorine$^{18}$. These isotopes can be introduced, for example, as cold kits and are reconstituted with the appropriate chemicals. The reconstituted compounds, after administration to the patient, are distributed within the body according to the physical and chemical properties of the specific agents as well as the moeity to which the radioactive label is attached.

These agents can be used for diagnosis in the brain as well as the systemic peripheral areas of the body; example include deposition of peripheral amyloid in the spleen, as well as in the brain in Alzheimer's disease. Attaching these radioactive agents, using methods well known in the art, to carrier molecules that pass the blood brain barrier, e.g. cymserine, can create specific neuropathology diagnostic agents.

An example is the use of technetium pertechnate used in brain imaging. This agent, combined with the highly selective butyrylcholinesterase inhibitors of the present invention will localize in certain sections of the brains such as the choroid plexus.

The optimal type of radiopharmaceutical has most of its energy in the form of gamma rays. The diagnostic equipment used in nuclear medicine has certain optimum detection energy levels. Most of the radioactive materials used for nuclear medicine are made by converting stable elements into radioactive forms. The conversion is performed by nuclear reactors or cyclotrons which bombard the stable elements with protons or neutron.

Advances in filmless detectors provide information abut the number of photons impinging on a sensitive element. This data, combined with the use of data processing algorithms have increased the power of medical imaging. The diagnostic imaging devices include computed tomography (CT), positron emission tomography (PET) Single Photon Emission Computed tomography (SPC), Digital Subtraction Angiography (DSA), Angiographic Imaging with synchotron radiation and Magnetic Resonance Imaging (MRI).

The principle isotopes used in imaging are carbon$^{11}$, oxygen$^{15}$, nitrogen$^{13}$. These agents are neutron poor, positron emitting isotopes. They are produced by a cyclotron and rapidly incorporated into the compounds of the present invention.

Thus, an embodiment of this aspect of the invention are compounds exhibiting highly selective butyrylcholinesterase inhibiting activity which are prepared incorporating a radiopharmaceutical agent thus providing an agent suitable for patient imaging for the detection for the presence of lesions or pathological states associated with Alzheimer's disease. Such agents can be introduced by sympathetic pathways known in the art. Thus, for example, the carbomyl moeity of the highly selective butyrylcholinesterase inhibitors can be provided as an α carbon$^{11}$ moeity by using the general procedures used by Bonnot, J. Label Comp. Radiopharm. 33 [4}, 277–284 (1993). The resulting compounds can be administered parenterally to the patient and will pass to the brain where they will selectively bind to any lesions or pathological states and can be detected by suitable imaging equipment such as a PET scan

REFERENCES:

1. Pei, X. F.; Greig, N. H.; Bi, S.; and Brossi, A. Preparstion and Selective Inhibition of Human Butyrylcholinrsterase by N$^1$-Phenethylnorphysostigmine Analogues. Med. Chem. Res. 1995, 5, 455–461.
2. Brzostowska, M.; He, X. S.; Greig, N. H.; Rapoport, S. I.; Brossi, A. Phenylcarbamates of (−)-Eseroline, (−)-N$^1$ Noreseroline and (−)-Physovenol: Selective Inhibitors of Acetyl and, or Butylcholinesterase. Med. Chem. Res. 1992, 2, 238–246.
3. Yu, Q. S.; Atack, J. R.; Rapoport, S. I.; and Brossi, A. Synthesis and Anticholinesterase Activity of (−)-Physostigmine, (−)-Eseramine, and Other N(−)-Substituted Analogues of (−)-Physostigmine. J. Med. Chem. 1997, 31, 2297–2300.
4. He, X. S.; Greig, N. H.; Rapoport, S. I.; Brossi, A. and Li, Y. Q. and Yu, Q. S. Thiaphysovenine and Carbamate Analogues: A Hew Class of Potent Inhibitors of Cholinesterases. Med. Chem. Res. 1992, 2, 229–237.
5. Yu, S. Q.; Liu, C.; Brzostowska, M.; Chrisey, L.; Brossi, A.; Greig, N. H.; Atack, J. R.; Soncrant, T. T.; Rapoport, S. I. and Radunz H. E. Physovenines: Efficient Synthesis of (−)-and (+)-Physovenine and Synthesis of Carbamate Analogues of (−)Physovenine. Anticholinesterase Activity and Analgesic Properties of Optically Active Physovenines. Hel. Cim. Acta 1991, 74, 761–766.
6. Yu, Q. S.; Pei, X. F.; Holloway, H. W.; Greig, N. H.; Brossi, A. Total Syntheses and Anticholinesterase Activities of (3aS)-N(8)-Norphysostigmine, (3aS)-N(8)-Norphenserine, Their Antipodal Isomers, and Other N(8)-Substituted Analogues. J. Med. Chem. 1997, 40, 2895–2901.
7. Yu, Q. S.; Holloway, H. W, Greig, N. H. and Brossi, A. Syntheses and Anticholinesterase Activities of (3aS)-N(1),N(8)-Norphysostigmine, (3aS)-N(1),N(8) Norphenserine, Their Antipodal Isomers, and Other Potential Metabolites of Phenserine. J. Med. Chem. 1997, 40, 2895–2901.
8. Atack, J. R.; Yu, Q. S.; Soncrant, T. T.; Brossi, A. and Rapoport, S. I. Comparative Inhibitory Effects of Various Physostigmine Analogs Against Acetyl- and Butylcholinesterases. J. Pharmacology and Experimental Therapeutics 1989, 249, 194–202.

What is claimed is:
1. The compound $N^8$-benzylnorcymserine.
2. The compound $N^8$-norcymserine.
3. The compound $N^1,N^8$-bisnorcymserine.
4. The compound $N^1,N^8$-bisbenylnorphysostigmine.
5. The compound $N^1,N^8$-bisbenzylnorphenserine.
6. The compound $N^1,N^8$-bisbenzylnorcymserine.

* * * * *

UNITED STATES PATENT AND TRADEMARK OFFICE
CERTIFICATE OF CORRECTION

PATENT NO.     : 6,410,747 B1
DATED          : June 25, 2002
INVENTOR(S)    : Nigel H. Greig et al.

It is certified that error appears in the above-identified patent and that said Letters Patent is hereby corrected as shown below:

Title page,
Item [73], Assignee, should read:
-- Axonyx, Inc., New York, N.Y. (US), and
   United States of America as represented by the Secretary, Department of Health and Human Services, Rockville, MD (US) --.

Signed and Sealed this

Twenty-seventh Day of December, 2005

JON W. DUDAS
*Director of the United States Patent and Trademark Office*